(12) United States Patent
Sera et al.

(10) Patent No.: US 11,560,346 B2
(45) Date of Patent: Jan. 24, 2023

(54) METHOD FOR PRODUCING ISOPROPYL ALCOHOL

(71) Applicant: TOKUYAMA CORPORATION, Yamaguchi (JP)

(72) Inventors: Akira Sera, Yamaguchi (JP); Masashi Shinagawa, Yamaguchi (JP); Masanari Ishizuki, Yamaguchi (JP)

(73) Assignee: TOKUYAMA CORPORATION, Yamaguchi (JP)

( * ) Notice: Subject to any disclaimer, the term of this patent is extended or adjusted under 35 U.S.C. 154(b) by 0 days.

(21) Appl. No.: 17/281,823

(22) PCT Filed: Oct. 3, 2019

(86) PCT No.: PCT/JP2019/039095
§ 371 (c)(1),
(2) Date: Mar. 31, 2021

(87) PCT Pub. No.: WO2020/071481
PCT Pub. Date: Apr. 9, 2020

(65) Prior Publication Data
US 2022/0017440 A1   Jan. 20, 2022

(30) Foreign Application Priority Data

Oct. 5, 2018 (JP) .............................. JP2018-189828
May 28, 2019 (JP) .............................. JP2019-099066

(51) Int. Cl.
- *C07C 29/04* (2006.01)
- *C07C 29/76* (2006.01)
- *C07C 29/80* (2006.01)

(52) U.S. Cl.
CPC .............. *C07C 29/04* (2013.01); *C07C 29/76* (2013.01); *C07C 29/80* (2013.01)

(58) Field of Classification Search
None
See application file for complete search history.

(56) References Cited

U.S. PATENT DOCUMENTS

| | | | | |
|---|---|---|---|---|
| 2,628,986 A | * | 2/1953 | Menn | C07C 29/74 568/915 |
| 5,868,906 A | * | 2/1999 | Adams | C07C 29/82 203/DIG. 16 |
| 6,733,637 B1 | * | 5/2004 | Burton | C07C 29/80 203/99 |
| 2015/0144557 A1 | * | 5/2015 | Ly | B01D 71/32 210/260 |

FOREIGN PATENT DOCUMENTS

| | | | | |
|---|---|---|---|---|
| CN | 103848718 A | * | 6/2014 | ............ C07C 29/76 |
| JP | 2003-535836 A | | 12/2003 | |
| JP | 2014-055120 A | | 3/2014 | |
| JP | 2016-073922 A | | 5/2016 | |
| WO | 2001/094284 A2 | | 12/2001 | |
| WO | 2018/135408 A1 | | 7/2018 | |

OTHER PUBLICATIONS

Seno, M. et al. "Aggregation of Ion-exchange Resin Particles" Jul. 1961 (Year: 1961).*
Machine translation WO2018135408A1, Jul. 26, 2018, pp. 1-28, (Year: 2018).*
Rohm-Haas "Ion Exchange Resins" Copyright 2010, pp. 1-2 (Year: 2010).*
Machine translation CN103848718A, Jun. 2014, pp. 1-8 (Year: 2014).*
International Search Report issued in International Application No. PCT/JP2019/039095, dated Dec. 17, 2019 (2 pages).
Written Opinion issued in International Application No. PCT/JP2019/039095, dated Dec. 17, 2019 (5 pages).

* cited by examiner

*Primary Examiner* — Medhanit W Bahta
(74) *Attorney, Agent, or Firm* — Osha Bergman Watanabe & Burton LLP

(57) ABSTRACT

A method for producing isopropyl alcohol is provided in which propylene is hydrated directly with water to produce isopropyl alcohol, the method including: a distillation step in which crude isopropyl alcohol is distilled; and a filtration step in which the isopropyl alcohol obtained in the distillation step is filtered through a filter having an ion-exchange group.

4 Claims, No Drawings

METHOD FOR PRODUCING ISOPROPYL ALCOHOL

TECHNICAL FIELD

The present invention relates to a method for producing isopropyl alcohol.

BACKGROUND ART

Metallic impurities included in various semiconductor processing liquids used in manufacturing processes for semiconductors are thought to cause, for example, a reduction in a semiconductor yield. Therefore, in order to enhance the yield, the metallic impurities included in the semiconductor processing liquids have been reduced by various methods. Recently, the metallic impurities are required to be further reduced due to the miniaturization of semiconductor design rules and an amount of the metallic impurities are required to be controlled to the order of ppt, especially for semiconductor design rules of a line width of 20 nm or less.

The metallic impurities included in the semiconductor processing liquids are divided broadly into two categories: metallic impurities mixed in a step of producing the semiconductor processing liquids and metallic impurities mixed in a storage, filling, or transportation step after production. Therefore, it is needed to not only reduce the metallic impurities mixed in a step of producing the semiconductor processing liquids but also the metallic impurities subsequently mixed in a storage, filling, or transportation step.

For example, Patent Document 1 describes a purification device including a filtration means with a filter having a particle removal diameter of 20 nm or less and a metal ion-adsorption means, as a method for reducing a metallic impurity in an organic solvent.

Patent Document 1: Japanese Unexamined Patent Application, Publication No. 2016-073922

DISCLOSURE OF THE INVENTION

Problems to be Solved by the Invention

The purification device described in Patent Document 1 can reduce the metallic impurity in the organic solvent to the order of ppt. However, the present inventors have conducted studies and found that, even though isopropyl alcohol is filtered through a filter having a particle removal diameter of 20 nm or less, the thus-filtered isopropyl alcohol includes a relatively large amount of organic impurities (in particular, organic impurities having a molecular weight of 100 or more and less than 140). The presence of such organic impurities in the isopropyl alcohol may reduce a semiconductor yield because the organic impurities may remain as, for example, particles on a wafer when the isopropyl alcohol is used as a semiconductor processing liquid.

Therefore, a problem of the present invention is to provide a method for producing isopropyl alcohol, the method capable of reducing contents of a metallic impurity and an organic impurity.

Means for Solving the Problems

Specific means for solving the above-mentioned problem include the following embodiments.

<1> A method for producing isopropyl alcohol through direct hydration of propylene with water, the method including:

a distillation step of distilling crude isopropyl alcohol; and
a filtration step of filtering isopropyl alcohol obtained from the distillation step with a filter having an ion-exchange group.

<2> The method for producing isopropyl alcohol according to <1>, wherein a contact time in the filtration step is 100 to 1000 seconds.

<3> The method for producing isopropyl alcohol according to <1> or <2>, wherein a differential pressure in the filtration step is 100 kPa or less.

<4> The method for producing isopropyl alcohol according to any one of <1> to <3>, wherein the filter having an ion-exchange group has a particle removal diameter of 1 nm or more and less than 20 nm.

<5> The method for producing isopropyl alcohol according to any one of <1> to <4>, wherein isopropyl alcohol which has been filtered includes a total of less than 5 ppb by mass organic impurities having a molecular weight of 100 or more and less than 140.

<6> The method for producing isopropyl alcohol according to any one of <1> to <5>, further including, prior to the filtration step, a pre-filtering step of filtering the isopropyl alcohol obtained from the distillation step with a filter having no ion-exchange group.

<7> The method for producing isopropyl alcohol according to <6>, wherein the isopropyl alcohol obtained from the distillation step is filtered more than once in the pre-filtration step.

Effects of the Invention

According to the present invention, a method for producing isopropyl alcohol, the method capable of reducing contents of a metallic impurity and an organic impurity can be provided. The isopropyl alcohol obtained by the method according to the present invention can be suitably used as a semiconductor processing liquid.

PREFERRED MODE FOR CARRYING OUT THE INVENTION

Embodiments of the present invention will be described in detail. As used herein, unless otherwise stated, the phrase "A to B" in the context of numerical values A and B shall mean "A or more and B or less". Even when only the numerical value B is appended with its unit in such a phrase, the unit shall also be applied to the numerical value A. Furthermore, as used herein including Examples, the units "%", "ppm", "ppb", and "ppt" representing a content are on a mass basis.

The method for producing isopropyl alcohol according to the present embodiment includes a distillation step of distilling, crude isopropyl alcohol and a filtration step or filtering isopropyl alcohol obtained from the distillation step with a filter.

(Crude Isopropyl Alcohol to be Purified)

The crude isopropyl alcohol refers to a composition including isopropyl alcohol as well as water, a metallic impurity, an organic impurity, and the like. The water, the metallic impurity, the organic impurity, and the like can be reduced by subjecting to the below-mentioned distillation step and filtration step, but the crude isopropyl alcohol refers to those which have not been subjected to the distillation step or the filtration step, in other words, from which the water, the metallic impurity, the organic impurity, and the like have not been reduced.

A content of the metallic impurity (amount of the metallic impurity) included in the crude isopropyl alcohol is not particularly limited. Among them, according to the method according to the present embodiment, crude isopropyl alcohol including a total of 1 to 1000 ppt of iron, chromium, and nickel can be suitably subjected to purification. Taking a purification efficiency in the method according to the present embodiment into consideration, crude isopropyl alcohol including a total of 1 to 100 ppt of iron, chromium, and nickel can be more suitably subjected to purification.

Furthermore, a content of the water (amount of the water) included in the crude isopropyl alcohol is not particularly limited. Among them, according to the method according to the present embodiment, crude isopropyl alcohol including 50 to 95% of water can be suitably subjected to purification. Taking a purification efficiency in the method according to the present embodiment into consideration, crude isopropyl alcohol including 50 to 94% of water can be more suitably subjected to purification.

In particular, in the method according to the present embodiment, crude isopropyl alcohol including a total of 1 to 1000 ppt (preferably 1 to 100 ppt) of iron, chromium, and nickel and 50 to 95% (preferably 50 to 94%) of water can be suitably subjected to purification.

Examples of the method for producing isopropyl alcohol include an acetone reduction method in which acetone is reduced, a Veba Chemie method which is a gas phase method using a fixed-bed catalyst, a Deutsche Texaco method which is a gas-liquid mixed phase method using a fixed-bed catalyst, and the like. However, in the present embodiment, crude isopropyl alcohol obtained through a direct hydration method is preferably purified.

The direct hydration method is a method in which propylene is directly reacted with water to thereby produce isopropyl alcohol and can be represented by the below-mentioned formula. The below-mentioned reaction can be performed in a reactor to thereby obtain crude isopropyl alcohol.

$$C_3H_6 + H_2O \rightarrow CH_3CH(OH)CH_3$$

Reaction conditions of the direct hydration method are not particularly limited, but a reaction pressure of 10 to 30 Mpa and a reaction temperature of 200 to 300° C. are preferable. Reaction conditions satisfying the above conditions can achieve both a yield enabling industrial production and durability of catalysts while suppressing generation of a reaction by-product (organic impurity). When the reaction temperature is more than 300° C., a reaction rate is increased but the reaction by-product tends to increase with the increase the reaction rate. Meanwhile, when a reaction temperature is less than 200° C., the reaction rate is decreased and the yield of isopropyl alcohol tends to decrease.

When isopropyl alcohol is produced by the direct hydration method, the reaction conditions (the reaction pressure, the reaction temperature, etc.) tend to be harsher. Furthermore, in the case of the direct hydration method, the isopropyl alcohol is synthesized from propylene and water and, therefore, an amount of water in the reactor larger than that of other production methods. Accordingly, the metallic impurity mixed from, for example, the reactor tends to increase compared to other production methods. Recently semiconductor manufacturing is becoming increasingly miniaturized and isopropyl alcohol having a higher purity is required to be used as a semiconductor processing liquid. For these reasons, in the present embodiment crude isopropyl alcohol obtained by the direct hydration method is preferably subjected to purification.

(Distillation Step)

Since the crude isopropyl alcohol includes water, metallic impurities, and reaction by-products (organic impurities), the crude isopropyl alcohol is firstly purified through distillation.

A distillation tower to be used in the distillation step and distillation conditions in the distillation step are not particularly limited. Taking boiling points of the organic impurities included in the crude isopropyl alcohol into consideration, distillation by which a low-boiling point organic matter having a boiling point lower than that of isopropyl alcohol is removed and distillation by which a high-boiling point organic matter having a boiling point higher than that of isopropyl alcohol is removed may be repeated. Repeating the distillations can further reduce the organic impurity. Moreover, an azeotropic distillation tower (e.g., a distillation tower in which distillation is performed with the addition of a relatively small amount of an aromatic solvent azeotropic with water (such as benzene, toluene, xylene, or the like)) is preferably added to further reduce the content of water.

In the distillation step, the crude isopropyl alcohol is preferably distilled until the content of water is 0.1 to 1000 ppm. In other words, post-distilled isopropyl alcohol preferably includes 0.1 to 1000 ppm of water. The content of water falling within the above-mentioned range allows the metallic impurity to be efficiently removed in the below-mentioned filtration step. Taking a filtration efficiency in the filtration step into consideration, the post-distilled isopropyl alcohol includes more preferably 0.1 to 100 ppm and further preferably 0.1 to 50 ppm of water.

Furthermore, in the distillation step, the crude isopropyl alcohol is preferably distilled until a total content of iron, chromium, and nickel is 1 to 1000 ppt. In other words, the post-distilled isopropyl alcohol preferably includes a total of 1 to 1000 ppt of iron, chromium, and nickel. The total content of iron, chromium, and nickel falling within the above-mentioned range allows these metallic impurities to be efficiently removed in the below-mentioned filtration step. Taking a filtration efficiency in the filtration step into consideration, the post-distilled isopropyl alcohol more preferably includes a total of 1 to 500 ppt and further preferably 1 to 100 ppt of iron, chromium, and nickel.

Note that, when the amount of the metallic impurity in the post-distilled isopropyl alcohol is, for example, of the order of ppb, the amount of the metallic impurity is difficult to reduce to the order of ppt even though the filtration step and the below-mentioned pre-filtration step are repeatedly performed. Therefore, the amount of the metallic impurity after the distillation step is preferably controlled to 1 to 100 ppt.

In particular, chromium is difficult to remove in the filtration step or the below-mentioned pre-filtration step since it is estimated that only a small portion of chromium is present in the form of a chromium particle or chromium oxide in the isopropyl alcohol. In this regard, isopropyl alcohol including 10 ppt or less or chromium can be stably produced by distilling crude isopropyl alcohol until a content of chromium is 10 ppt or less while adjusting distillation conditions such as the number of theoretical plates, a temperature at the top of the column, a temperature at the bottom of the column, and a reflux ratio.

Moreover, from the viewpoints of filtration efficiency in the filtration step, a usable life of a filter, and the like, the crude isopropyl alcohol is preferably distilled in the distillation step until a content of particles having a particle diameter of 0.3 μm or less is 1 to 200 particles per mL of isopropyl alcohol. In other words, 1 mL of the post-distilled isopropyl alcohol preferably includes 1 to 200 particles having a particle diameter of 0.3 μm or less. Note that, the content of the particles in isopropyl alcohol can be measured by a particle counter.

Examples of the organic impurity included in the post-distilled isopropyl alcohol include organic impurities having a molecular weight of 100 or more and less than 140. The organic impurities are estimated to be mainly oxygen-containing hydrocarbon compounds. The presence of such organic impurities in the isopropyl alcohol may reduce a semiconductor yield because the organic impurities may remain as, for example, particles on a wafer when the isopropyl alcohol is used as the semiconductor processing liquid. Therefore, the organic impurities are preferably removed as much as possible. In the present embodiment, such organic impurities can be removed in the below-mentioned filtration step. From the viewpoint, for example, of filtration efficiency in the filtration step, a total content of the organic impurities having a molecular weight of 100 or more and less than 140 included in the post-distilled isopropyl alcohol is preferably 5 to 100 ppb and more preferably 5 to 10 ppb. Note that, this content of the organic impurities can be determined by concentrating the isopropyl alcohol and measuring using gas chromatography (GC).

The isopropyl alcohol obtained from the distillation step as described above is subjected to the filtration step. For example, the isopropyl alcohol obtained from a distillation tower is directly transferred through, for example, a pipe to a filtration device and subjected to the filtration step. Thus, an increase in the metallic impurity can be suppressed by directly filtering isopropyl alcohol immediately after the distillation without leaving to stand isopropyl alcohol that is water-soluble and hygroscopic.

(Filtration Step)

In the filtration step, the isopropyl alcohol obtained from the distillation step is filtered through a filter to thereby remove the metallic impurity, the organic impurity, and the like. The filtration step can be performed, for example, by locating a filter in a transfer pipe for transferring the isopropyl alcohol which has been purified in the distillation step into a storage tank.

The filter in the filtration step is preferably a resin filter made of 6-nylon, 6, 6-nylon, polyethylene, polypropylene, polystyrene, a fluororesin, or the like from the viewpoint of a more efficient reduction in the metallic impurity. Among them, a filter made of a fluororesin is more preferable and a filter made of polytetrafluoroethylene (PTFE) is further preferable. In particular, in the present embodiment, from the viewpoint of a more efficient reduction in the organic impurity, a filter on which surface an ion-exchange film having an ion-exchange group such as an acidic group or an alkaline group is formed is suitably used. An ion-exchange capacity of a surface of the filter having an ion-exchange group is preferably 0.1 to 10 milliequivalents and more preferably 0.3 to 8 milliequivalents.

The filter in the filtration step may be those commercially available. Specifically, filters manufactured by Enteqris, Inc., Pall Corporation, or the like may be used. These filters may be appropriately selected according to the desired purity of isopropyl alcohol. One type of filter may be used alone or one type of filters having different particle removal diameters may be tandemly-arrayed. Furthermore, multiple types of filters may be used in combination. For example, multiple types of filters may be tandemly-arrayed.

In the filtration step, a contact time between the filter and the isopropyl alcohol is preferably 100 to 1000 seconds, more preferably 150 to 1000 seconds, further preferably 300 to 1000 seconds, and particularly preferably 500 to 1000 seconds. The contact time of 100 seconds or more can further reduce a content of an impurity, particular, of an organic impurity. Furthermore, the contact time of 1000 seconds or less can further suppress the filtration efficiency from deteriorating. Therefore, the contact time falling within the above-range allows the metallic impurity, the organic impurity, and the like included in the isopropyl alcohol to be efficiently removed. Note that, the contact time is defined according to the expression below:

Contact time (sec)=filter volume (mL)/flow rate isopropyl alcohol (mL/sec).

When the isopropyl alcohol is passed through the filter, a differential pressure, a difference pressure between an inlet and an outlet of the filter, is preferably 100 kPa or less. It is thought that the lower the differential pressure is, the higher the collection efficiency of metallic impurity and the organic impurity is. From the viewpoints of a further reduction in the metallic impurity and the organic impurity and enhancement of productivity, the differential pressure is more preferably to 50 kPa and further preferably 1 to 2 kPa.

Furthermore, a particle removal diameter of the filter in the filtration step is preferably 1 nm or more and less than 20 nm. When the particle removal diameter is too small, there is a trend that the differential pressure is increased and the filtration efficiency deteriorates. Meanwhile, when the particle removal diameter is too large, an effect of reducing the metallic impurity and the organic impurity tends to deteriorate. Taking the effect of reducing the metallic impurity and the organic impurity, and industrial production into consideration, the particle removal diameter of the filter is preferably 1 to 15 nm. Note that, the filter having a particle removal diameter of "A (nm)" means that 99.9% or more of particles having a particle diameter of "A (nm)" or more are collected.

The filter having the particle removal diameter of 1 to 15 nm and the differential pressure of 1 to 25 kPa has a particularly enhanced effect of removing the metallic impurity and the organic impurity. When the isopropyl alcohol of interest is produced by the direct hydration method and distilled until the content of water is 0.1 to 1000 ppm (more preferably 0.1 to 100 ppm, further preferably 0.1 to 50 ppm, and particularly preferably 0.1 to 30 ppm) and the content of the metallic impurity is 7 to 1.000 ppt (more preferably 7 to 50) ppt, further preferably 7 to 100 ppt, and particularly preferably 8 to 100 ppt), a filtration effect under the above-mentioned conditions of the particle removal diameter and the differential pressure is remarkable.

(Post-Purified Isopropyl Alcohol)

Isopropyl alcohol including 0.001 to 5 ppt of chromium, a total of 0.001 to 10 ppt of iron, chromium, and nickel, and 0.1 to 100 ppm of water can be obtained by producing as described above. This isopropyl alcohol is suitably used as the semiconductor processing liquid due to its nigh purity.

Furthermore, isopropyl alcohol having a lower content of the organic impurities can be obtained by using the filter having an ion-exchange group in the filtration step. Specifically, the total content of the organic impurities having a molecular weight of 100 or more and less than 140 included in the isopropyl alcohol may be less than 5 ppb.

Note that, water is believed to have a less adverse effect than the metallic impurity even though included in the semiconductor processing liquid, but, when included in the isopropyl alcohol, may act as a catalyst in a reaction of the organic impurities and may increase the metallic impurity in some members with which the isopropyl alcohol comes into contact. Therefore, the content of water is more preferably 50 ppm or less and further preferably 10 ppm or less. Meanwhile, taking industrial production into consideration, 0.1 ppm or more of water is generally included in the isopropyl alcohol.

(Pre-Filtration Step))

The method according to the present embodiment may include, prior to the filtration step, a pre-filtration step of filtering the isopropyl alcohol obtained from the distillation step with filter. In the pre-filtration step, the number or filtrations of isopropyl alcohol with the filter is not particularly limit but the filtration is preferably performed more than once from the viewpoint of a further reduction in the metallic impurity and the organic impurity More specifically, the isopropyl alcohol obtained from the distillation step is preferably subject to cycle filtration by circulating and repeatedly passing the isopropyl alcohol through the filter.

Such a cycle filtration may be performed by transferring the post-distilled isopropyl alcohol into a storage tank equipped with a circulating pump and a circulating pipe and circulating the isopropyl alcohol through at least one filter located in the circulating pipe.

A filter configuration in the cycle filtration is not particularly limited, but usually a three-staged filter configuration is preferable since the larger the number of the filters is, the greater the pressure loss is and the lower the productivity is. In particular, a first filter has preferably a particle removal diameter of 500 to 2000 nm and more preferably 750 to 1250 nm. Furthermore, a second filter has preferably a particle removal diameter of 30 to 100 nm and more preferably 40 to 60 nm. Furthermore, a third filter has preferably a particle removal diameter of 1 to 20 urn and more preferably 5 to 1.5 nm. Thus, both removal of impurities and productivity can be achieved by locating the filters so as to decrease the particle removal diameter stepwise.

A flow rate upon the cycle filtration is not particularly limited, but the flow rate of 3 to 5 m$^3$/hr is usually enough, taking an energy cost of the circulating pump into consideration. Furthermore, a period of circulation is not particularly limited, but 0.5 to 7 days are usually enough, taking a contamination risk such as elution from the tank or the filter due to long-term storage into consideration.

Note that, the filter in the pre-filtration step is preferably a filter having no ion-exchange croup. When the cycle filtration is performed as described above, the filter and the isopropyl alcohol repeatedly come into contact with each other. Therefore, when the filter having an ion-exchange group is used, this ion-exchange group may cause the organic impurity to react with the isopropyl alcohol or with each other. Therefore, in the pre-filtration step, the filter having no ion-exchange group is preferably used.

(Other Suitable Aspects)

In the present embodiment, a pipe for transferring isopropyl alcohol (transfer pipe), a container for storing isopropyl alcohol, and the like are preferably subjected to a passivation treatment at a liquid contact portion to be contacted with isopropyl alcohol. When the liquid contact portion to be contacted with isopropyl alcohol is subjected to the passivation treatment, an increase in the amount of the metallic impurity in the isopropyl alcohol can be suppressed in the storage, filling, or transportation step.

The passivation treatment preferably forms a passivation layer having a film thickness of 2 to 500 nm, more preferably a passivation layer having a film thickness of 2 to 100 nm, and further preferably a passivation layer having a film thickness of 2 to 20 nm on a surface of a stainless steel material at the liquid contact portion to be contacted with isopropyl alcohol.

A method for forming the passivation layer is not particularly limited, but a suitable passivation layer may be formed by subjecting to an electropolishing step, a washing step with an inorganic acid, and a heating step. In particular, atomic concentrations of a chromium atom and a silicon atom on an outermost surface of the passivation layer are more easily adjusted by performing the electropolishing step, the washing step with an inorganic acid, and the heating step in this order.

The electropolishing step is a polishing step with application of electricity by passing an electrolyte solution through the liquid contact portion and any known method may be employed. For example, electricity may be applied to the liquid contact portion while passing phosphoric acid/sulfuric acid through the Liquid contact portion.

In the heating step, the liquid contact portion is heated to thereby remove an oxide layer, in particular, a chromium oxide layer, and grow a dense iron oxide layer from a surface of the passivation layer. Tiflis beating step can adjust a film thickness of the chromium oxide layer, in other words, can adjust an atomic concentration of a chromium atom or a silicon atom on the outermost surface of the passivation layer. In particular, the film thickness of the chromium oxide layer can be effectively adjusted by performing the heating step after the liquid contact portion is washed with an inorganic acid.

A heating atmosphere is preferably an oxidative atmosphere including air. Heating under the oxidative atmosphere can promote growth of an oxide film. Furthermore, heating temperature is preferably 300 to 450° C. and more preferably 300 to 400° C.

A heating time is not particularly limited and may be determined so that the atomic concentration of a chromium atom on the outermost surface of the passivation layer is 0.1 to 10 atom %. At that time, in addition to the above condition, the heating time is preferably determined so that the atomic concentration of a silicon atom is 0.1 to 10 atom %. Usually, from the viewpoint of economic efficiency, the heating time is preferably 0.5 to 10 hours and more preferably to 3 hours. The heating time falling within the above range can produce a member on which the iron oxide film is sufficiently grown and from which a decreased amount of metal eluted.

An increase in the metallic impurity can be further suppressed by including the distillation step in a production process of isopropyl alcohol, directly passing a distillate obtained from the distillation step through a filter, and subjecting the liquid contact portion in the storage, filling, or transportation step to a specific passivation treatment.

EXAMPLES

Hereinafter, the present invention will be more specifically described with reference to Examples, but the present invention is not limited to these Examples.

Amounts of a metallic impurity and water were measured as follows.

(Method for Measuring Amount of Metallic Impurity)

A metallic impurity included in isopropyl alcohol was quantified using an inductively coupled plasma-mass spectrometer (ICP-MS) as follows. About 500 mL of isopropyl alcohol which had been purified under conditions described in the Examples and the Comparative Examples was collected in a round-bottomed flask, concentrated to dryness using a rotatory evaporator, and then collected into about 25 mL of 0.1 N nitric acid in two portions. For the thus-collected 0.1 N nitric acid solution, an amount of metal elution was quantified using the ICP-MS. At that time, a concentration rate was calculated from a ratio of a weight of isopropyl alcohol before concentration to a weight of 0.1 N nitric acid solution after collection and was used to convert the amount of metal elution into an amount of the metallic impurity per weight of isopropyl alcohol.
(Method for Measuring Amount of Water)
Device: Karl-Fisher moisture meter A0-7 (manufactured by HIRANUMA Co., Ltd.)
Method: 0.25 g of a measurement sample and 0.75 g of dehydrated acetonitrile were mixed in a glove box having a dew-point of −80°C or less. Then, 0.5 g of the resultant mixed solution was collected with a sufficiently dried Terumo Syringe (trade name, 2.5 mL) in the glove box and measured for the amount of water using the Karl-Fisher moisture meter.

Furthermore, for the organic impurity, a measurement sample was prepared according to the below-mentioned concentration method and then qualitatively and quantitatively analyzed.
(Concentration Method of Isopropyl Alcohol)
Two liters of isopropyl alcohol was distilled for 12 hours and concentrated to 7 mL (concentration rate: about 300-fold) using a device for precision distillation under reduced pressure, equipped with a filling and having the number of theoretical plates of 2 to 30 and a temperature at the top of a distillation tower of 15 to 20° C. The resultant concentrate was placed in a vial and further concentrated by passing nitrogen over a liquid surface to thereby prepare 2 mL of a concentrate (concentration rate: 1000-fold).
(Method for Measuring Organic Impurity: Qualitative Analysis)
An organic impurity included in isopropyl alcohol was measured using a gas chromatograph-mass spectrometer (GC-MS) under the following measurement conditions.
—Measurement Conditions—
Device: 7890B/5977B (manufactured by Agilent Technologies)
Analytical column: CP-Wax-57CB (50 m×0.32 mm, 1.2 μm)
Column temperature: 30° C. (hold for 3 min)→ramp at 5° C./min→100° C.→ramp at 10° C./min→200° C. (hold for 5 min) Carrier gas: helium
Flow rate of carrier gas: 3 mL/min
Inlet temperature: 200° C.
Sample injection method: pulsed splitless method
Injection pulse pressure: 90 psi (2 min)
Split vent flow rate: 50 mL/min (2 min)
Use of gas saver: 20 mL/min (5 min)
Transfer line temperature: 200° C.
Ion source and quadrupole temperatures: 230° C., 150° C.
Scanning ion: m/Z=20 to 400
Isopropyl alcohol was concentrated according to the above-mentioned concentration method. When a peak was confirmed, library search was performed based on the mass spectrum of the peak to identify the structure. For a substance of which structure was not identified from the mass spectrum of the confirmed peak, it was confirmed that an impurity is present at the corresponding retention time.
(Method for Measuring Organic Impurity: Quantitative Analysis)
Reference materials for the compound of which structure had been identified according to the above-mentioned qualitative analysis method were prepared and quantified for peak areas in advance. These peak areas were compared to that of the compound which had been detected in the qualitative analysis to thereby quantify a concentration of the compound using a selected ion monitoring (SIM) method. For a compound of which structure was not able to be identified and a compound of which reference materials were not available, an area or hexadecane on a total ion chromatogram was used as a reference for quantitation. An impurity in isopropyl alcohol was quantified under the same conditions as the conditions described under the title (Method for measuring organic impurity: qualitative analysis) with the addition of a selected ion monitoring (SIM) mode without concentrating the isopropyl alcohol. A SIM monitoring ion was as follows.
—SIM Monitoring Ion—
Group 1 initiation time: 12.7 min, m/Z: 69, 83, 8, 101, 115, 131 (dwell 30)

Example 1

(Production of Crude Isopropyl Alcohol)
Propylene including, as impurities, 39972 ppm of propane, 20 ppm of ethane, 8 ppm of butene, 0.1 ppm or less of pentene, and 0.1 ppm or less of hexene was prepared as a raw material. Furthermore, water that had been adjusted to pH 3.0 by adding phototungstic acid serving as an acid was prepared as a raw material. A reactor having an internal volume of 10 L was charged with water heated to 11.0° C. at a feed rate of 18.4 kg/h (20 L/h, from a density of 920 k, m$^3$) and propylene at a feed rate of 1.2 kg/h.

The propylene and the water were reacted within the reactor at a reaction temperature of 280° C. and a reaction pressure of 250 atm to thereby obtain isopropyl alcohol. A reaction product including the thus-produced isopropyl alcohol was cooled to 140° C. and the pressure was reduced to 18 atm. Thus, propylene dissolved in water included in the reaction product was collected as a gas. The thus-collected propylene was placed into a propylene collection drum for recycling as a raw material. At that time, a conversion of the fed propylene was 84.0%, a selectivity of the propylene to the isopropyl alcohol was 99.2%, and a content of the isopropyl alcohol in the resultant reaction mixture was 7.8%. Furthermore, a content of water in the resultant reaction mixture was 92.2%.
(Distillation Step)
The resultant crude isopropyl alcohol was subjected to distillation including dehydration to thereby obtain isopropyl alcohol with a less amount of impurities. A content of water in the post-distilled isopropyl alcohol was 12 ppm. Each of contents of iron, chromium, and nickel in the post-distilled isopropyl alcohol is described in Table 2.
(Pre-Filtration Step)
The post-distilled isopropyl alcohol was transferred to a tank having a volume of 200 L and equipped with a circulating pump and a circulating pipe. After transfer to the tank, cycle filtration was performed through a PTFE filter having a particle removal diameter of 1000 nm, a PTFE filter having a particle removal diameter of 50 nm, and PTFE filter having a particle removal diameter of 10 nm located in the circulating pipe at a flow rate of 4 m$^3$/hr for 1 day (pre-filtration step). Filtration conditions in the pre-filtration step are described in Table 1. Furthermore, each of contents of iron, chromium, and nickel in the post-prefiltered isopropyl alcohol is described in Table 2.
(Filtration Step)
The post-prefiltered isopropyl alcohol was filtered by passing through a PTFE filter having an ion-exchange group and a particle removal diameter of 5 nm (ion-exchange group: sulfone group, ion-exchange capacity: 0.48 to 4.3 milliequivalents)) and a PTFE filter having no ion-exchange group and a particle removal diameter of 2 nm (filtration step). At that time, a flow rate was adjusted to 1 mL/sec so that a contact time between isopropyl alcohol and the filter having an ion-exchange group was 720 seconds. Note that, a differential pressure during use of the filter was 50 kPa. Filtration conditions in the filtration step are described in Table 1. Furthermore, each of contents of iron, chromium, and nickel in the post-filtered isopropyl alcohol is described in Table 2.

The organic impurity in the post-filtered isopropyl alcohol was qualitatively analyzed as mentioned above and, as a result, the presence of peaks at retention times of 23.6 min and 25.0 min on a gas chromatogram (GC), that is, high-concentration impurities (hereinafter referred to as "specific organic impurities" in some cases) was confirmed. The organic impurity corresponding to the peak at the retention time or 23.6 min had a molecular weight of 116 and the organic impurity corresponding to the peak at the retention time of 25.0 min had a molecular weight of 130. These peaks were quantitatively analyzed and the results for contents of the specific organic impurities are described in Table 3.

Example 2

The operation was performed in the same manner as in Example 1, except that the filtration conditions in the filtration step were changed as described in Table 1. Each of contents of iron, chromium, and nickel in the post-filtered isopropyl alcohol is described in Table 2 and the contents of the specific organic impurities are described in Table 3.

Example 3

The operation was performed in the same manner as in Example 1, except that the pre-filtration step was not performed and the filtration conditions in the filtration step were changed as described in Table 1. Each of contents of iron, chromium, and nickel in the post-filtered isopropyl alcohol is described in Table 2 and the contents of the specific organic impurities are described in Table 3.

Comparative Example 1

The operation was performed in the same manner as in Example 1, except that the filtration conditions in the filtration step were changed as described in Table 1. Each of contents of iron, chromium, and nickel in the post-filtered isopropyl alcohol is described in Table 2 and the contents of the specific organic impurities are described in Table 3.

Comparative Examples 2,3

The operation was performed in the same manner as in Example 1, except that the pre-filtration step was not performed and the filtration conditions in the filtration step were changed as described in Table 1. Each of contents of iron, chromium, and nickel in the post-filtered isopropyl alcohol is described in Table 2 and the contents of the specific organic impurities are described in Table 3.

TABLE 1

| | Filtration step | | | | | | |
|---|---|---|---|---|---|---|---|
| | Pre-filtration step Particle removal diameter of filter | | | Particle removal diameter of filter | | | |
| | | | | With ion-exchange group | Without ion-exchange group | Contact time | Flow rate | Differential pressure |
| Example 1 | 1000 nm | 50 nm | 10 nm | 5 nm | 2 nm | 720 sec | 1 mL/sec | 50 kPa |
| Example 2 | 1000 nm | 50 nm | 10 nm | 5 nm | 2 nm | 180 sec | 4 mL/sec | 50 kPa |
| Comparative Example 1 | 1000 nm | 50 nm | 10 nm | | 2 nm | 120 sec | 6 mL/sec | 50 kPa |
| Comparative Example 2 | | | | | 10 nm | 120 sec | 6 mL/sec | 50 kPa |
| Comparative Example 3 | | | | | 2 nm | 120 sec | 6 mL/sec | 50 kPa |
| Example 3 | | | | 5 nm | | 120 sec | 6 mL/sec | 50 kPa |

TABLE 2

| | Amount of metallic impurities (ppt) | | | | | | | | |
|---|---|---|---|---|---|---|---|---|---|
| | Post-distilled | | | Post-prefiltered | | | Post-filtered | | |
| | Fe | Cr | Ni | Fe | Cr | Ni | Fe | Cr | Ni |
| Example 1 | 19.2 | 3.9 | 4.1 | 5.4 | 3.6 | 4.1 | 1.4 | 3.5 | 3.8 |
| Example 2 | 17.2 | 2.3 | 3.0 | 5.2 | 2.8 | 2.8 | 1.4 | 2.5 | 3.1 |
| Comparative Example 1 | 20.3 | 4.4 | 3.6 | 6.3 | 4.1 | 3.3 | 1.5 | 4.2 | 3.3 |
| Comparative Example 2 | 19.1 | 3.3 | 3.4 | 20.1 | 3.4 | 3 | 3.6 | 2.9 | 3.1 |
| Comparative Example 3 | 18.5 | 3.1 | 2.9 | 19.1 | 2.9 | 3 | 2.5 | 3 | 3.2 |
| Example 3 | 21.3 | 2.8 | 2.6 | 20.7 | 3 | 2.3 | 10.1 | 2.7 | 2.5 |

TABLE 3

| | Amounts of specific organic impurities (ppb) | |
|---|---|---|
| | GC retention time 23.6 min | GC retention time 25.0 min |
| Example 1 | <0.3 | <0.3 |
| Example 2 | 0.8 | 0.4 |
| Comparative Example 1 | 1.5 | 0.8 |
| Comparative Example 2 | 2.5 | 1.3 |
| Comparative Example 3 | 2.4 | 1.2 |
| Example 3 | 1.4 | 0.6 |

As clear from the results in Tables 2 and 3, the amounts of metallic impurities could be reduced by performing the filtration step after the distillation step. In particular, the organic impurities having a molecular weight of 100 or more and less than 140 could be efficiently removed by using the filter having an ion-exchange group.

The contents of Japanese Patent Application No. 2018-189878 filed on Oct. 5, 2018 and Japanese Patent Application No. 2019-99066 filed on May 28, 2019 are incorporated herein by reference in its entirety.

The invention claimed is:

1. A method for producing isopropyl alcohol through direct hydration of propylene with water, the method comprising:
   a distillation step of distilling crude isopropyl alcohol; and
   a filtration step of filtering isopropyl alcohol obtained from the distillation step with a filter having an ion-exchange group,
   wherein:
   the filter having an ion-exchange group comprises an ion-exchange film having an ion-exchange group,
   a contact time in the filtration step is 100 to 1000 seconds,
   a differential pressure in the filtration step is 100 kPa or less, and
   the filter having an ion-exchange group has a particle removal diameter of 1 nm or more and less than 20 nm.

2. The method for producing isopropyl alcohol according to claim 1, wherein isopropyl alcohol which has been filtered comprises a total of less than 5 ppb by mass of organic impurities having a molecular weight of 100 or more and less than 140.

3. The method for producing isopropyl alcohol according to claim 1, further comprising, prior to the filtration step, a pre-filtering step of filtering the isopropyl alcohol obtained from the distillation step with a filter having no ion-exchange group.

4. The method for producing isopropyl alcohol according to claim 3, wherein the isopropyl alcohol obtained from the distillation step is filtered more than once in the pre-filtering step.

* * * * *